(12) United States Patent
Zeng et al.

(10) Patent No.: US 7,464,580 B2
(45) Date of Patent: Dec. 16, 2008

(54) IONIC LIQUID HIGH TEMPERATURE GAS SENSORS

(75) Inventors: Xiangqun Zeng, Rochester, MI (US);
Lei Yu, Auburn Hills, MI (US); Rex Xiaofeng Ren, Middletown, CT (US)

(73) Assignee: Oakland University, Rochester, MI (US)

( * ) Notice: Subject to any disclaimer, the term of this patent is extended or adjusted under 35 U.S.C. 154(b) by 44 days.

(21) Appl. No.: 11/522,833

(22) Filed: Sep. 18, 2006

(65) Prior Publication Data

US 2007/0068222 A1    Mar. 29, 2007

Related U.S. Application Data

(60) Provisional application No. 60/720,581, filed on Sep. 26, 2005.

(51) Int. Cl.
*G01N 29/02* (2006.01)
(52) U.S. Cl. .................................. 73/24.01; 73/24.06
(58) Field of Classification Search ............... 73/24.01, 73/24.06
See application file for complete search history.

(56) References Cited

U.S. PATENT DOCUMENTS

| | | | |
|---|---|---|---|
| 3,327,519 A * | 6/1967 | Crawford | 73/24.06 |
| 4,236,893 A | 12/1980 | Rice | |
| 4,242,096 A | 12/1980 | Oliveira et al. | |
| 4,246,344 A | 1/1981 | Silver, III | |
| 4,314,821 A | 2/1982 | Rice | |
| 4,735,906 A | 4/1988 | Bastiaans | |
| 4,788,466 A | 11/1988 | Paul et al. | |
| 4,999,284 A | 3/1991 | Ward et al. | |
| 5,117,192 A | 5/1992 | Hurd | |
| 5,201,215 A | 4/1993 | Granstaff et al. | |
| 5,233,261 A | 8/1993 | Wajid | |
| 5,282,925 A | 2/1994 | Jeng et al. | |
| 5,314,830 A | 5/1994 | Anderson et al. | |
| 5,484,626 A | 1/1996 | Storjohann et al. | |
| 5,616,827 A | 4/1997 | Simmermon et al. | |
| 5,622,826 A | 4/1997 | Varma | |
| 5,706,840 A | 1/1998 | Schneider | |

(Continued)

FOREIGN PATENT DOCUMENTS

WO    WO 0351894    6/2003

OTHER PUBLICATIONS

Iichat Goubaidoulline et al. "Organic Vapor Sensing with Ionic Liquids Entrapped in Alumina Nanopores on Quartz Crystal Resonators" Analytical Chemistry Jan. 2005, web published on Dec. 13, 2004, vol. 77, pp. 615-619.*

(Continued)

*Primary Examiner*—Michael Cygan
(74) *Attorney, Agent, or Firm*—Ian C. McLeod

(57) ABSTRACT

An ionic liquid piezoelectric gas sensor for the detection of polar and nonpolar organic vapors. The gas sensor can operate at high temperatures with a fast linear response which is also reversible. At high temperatures, the frequency change ($\Delta f$) versus concentration (C) curve mirrors the Henry's gas law, such that the concentration of a gas sample in liquid solvent is proportional to the concentration or partial pressure of the sample in gas phase. The gas sensor can be used for quantitative analysis of gas vapors and determination of Henry constants.

20 Claims, 6 Drawing Sheets

U.S. PATENT DOCUMENTS

| | | | |
|---|---|---|---|
| 5,795,993 | A | 8/1998 | Pfeifer et al. |
| 5,885,402 | A | 3/1999 | Esquibel |
| 5,932,953 | A | 8/1999 | Drees et al. |
| 6,087,187 | A | 7/2000 | Wiegland et al. |
| 6,106,149 | A | 8/2000 | Smith |
| 6,190,035 | B1 | 2/2001 | Smith |
| 6,319,674 | B1 | 11/2001 | Fulcrand et al. |
| 6,368,877 | B1 | 4/2002 | Zhang et al. |
| 6,439,765 | B2 | 8/2002 | Smith |
| 6,475,808 | B1 | 11/2002 | Wagner et al. |
| 6,475,809 | B1 | 11/2002 | Wagner et al. |
| 6,492,601 | B1 | 12/2002 | Cain et al. |
| 6,494,077 | B2 * | 12/2002 | Aoyama et al. ............ 73/23.34 |
| 6,647,764 | B1 | 11/2003 | Paul et al. |
| 6,706,977 | B2 | 3/2004 | Cain et al. |
| 6,848,299 | B2 | 2/2005 | Paul et al. |
| 6,852,229 | B2 | 2/2005 | Mehnert et al. |
| 6,890,486 | B2 | 5/2005 | Penelle |
| 2002/0094531 | A1 | 7/2002 | Zenhausem |
| 2002/0142477 | A1 | 10/2002 | Lewis et al. |
| 2003/0049204 | A1 | 3/2003 | Leyland-Jones |
| 2003/0053950 | A1 | 3/2003 | Leyland-Jones |
| 2003/0068273 | A1 | 4/2003 | Leyland-Jones |
| 2003/0072710 | A1 | 4/2003 | Leyland-Jones |
| 2003/0073133 | A1 | 4/2003 | Leyland-Jones |
| 2003/0077222 | A1 | 4/2003 | Leyland-Jones |
| 2003/0204041 | A1 | 10/2003 | Laas et al. |
| 2004/0054231 | A1 | 3/2004 | Abbott et al. |
| 2004/0262578 | A1 | 12/2004 | Wasserscheid et al. |
| 2005/0005840 | A1 | 1/2005 | Bonrath et al. |
| 2006/0278536 | A1 * | 12/2006 | Burrell et al. ............... 205/775 |

OTHER PUBLICATIONS

Chengdu Liang et al. "Ionic Liquids: A New Class of Sensing Materials for Detection of Organic Vapors Based on the Use of a Quartz Crystal Microbalance" Analytical Chemistry May 2002, vol. 74, pp. 2172-2176.*

Xiangqun Zeng et al. "Ionic Liquid High-Temperature Gas Sensor Array" Analytical Chemistry Oct. 1, 2006, web published Sep. 6, 2006, vol. 78, pp. 6980-6989.*

Lei Yu et al. "Ionic liquid high temperature gas sensors", Chem. Commun., web published Mar. 10, 2005, pp. 2277-2279.*

Tsang et al., J. Phys. Chem. B., 2001, 105, 5737-5742.

Kaltenpoth et al., Anal. Chem., 2003, 75, 4756-4765.

Dutta et al., J. Phys. Chem. B., 1999, 103, 4412-4422.

Zhu et al., Anal. Chem., 2002, 74, 120-124.

Simon et al., J. Comb. Chem., 2002, 4, 511-515.

Hu et al., J. Phys. Chem. B, 2004, 108, 11214-11218.

Wang et al., J. Am. Chem. Soc., 2003, 125, 16176-16177.

Dutta et al., Chem. Mater., 2004, 16, 5198-5204.

Grate et al., Anal. Chem., 1993, 65, 987A.

Jarrett and Finklea, Anal. Chem., 1999, 71, 353.

Shinar et al., Anal. Chem., 2000, 72, 5981.

Zellers et al., Anal. Chem., 1995, 67, 1092.

Patrash and Zellers, Anal. Chem., 1993, 65, 2055.

Liang et al., Anal. Chem., 2002, 74, pp. 2172-2176.

Yang et al., Nature Materials 1: 253-257 (2002).

K.R. Seddon, J. Chem Tech. Biotech., 1997, 68, 315-316.

M. Albrecht, M. Schlupp, J. Bargon and G. Van Koten, Chem. Commun., 2001, 1874.

R.X. Ren and J. X. Wu, Org. Lett., 2001, 3, 3727.

J.W. Grate and M. Klusty, Anal. Chem., 1991, 63, 1719.

J. W. Grate et al., Anal. Chem., 1992, 64, 610.

A. Janshoff, et al., Angew Chem. Int. Ed., 2000, 39, 4004-4032.

* cited by examiner

IONIC LIQUID HIGH TEMPERATURE GAS SENSORS

CROSS-REFERENCE TO RELATED APPLICATIONS

This application claims benefit of Provisional Application No. 60/720,581, filed Sep. 26, 2005, which is incorporated herein by reference in its entirety.

STATEMENT REGARDING FEDERALLY SPONSORED RESEARCH OR DEVELOPMENT

This research was supported by grants from the National Institutes of Health (NIH R33EB000672-02). The U.S. government has certain rights to this invention.

BACKGROUND OF THE INVENTION (1) Field of the Invention

The present invention relates generally to gas sensors, and more particularly to ionic liquid piezoelectric gas sensors. Specifically, the present invention relates to ionic liquid piezoelectric gas sensors which are capable of detecting both polar and nonpolar organic vapors at high temperature and which have a fast linear and reversible response.

(2) Description of the Related Art

Identifying and correcting emissions from high-polluting vehicles requires small sensors working at high temperatures to monitor pollutants in exhaust gas or leaking fuels (Tsang et al., *J. Phys. Chem.* B, 2001, 105, 5737-5742; Kaltenpoth et al., *Anal. Chem.*, 2003, 75, 4756-4765). High temperature gas sensing is conventionally achieved by using semi-conductive metal oxides, such as $SnO_2$ and $TiO_2$ (Dutta et al., *J. Phys. Chem.* B, 1999, 103, 4412-4422; Ikohura and Watson, *The Stannic Oxide Gas Sensor*; CRC Press: Boca Raton, Fla., 1994; Zhu et al., *Anal. Chem.*, 2002, 74, 120-124). The resistance of metal oxides changes in the presence of organic vapors, CO or $H_2$. It takes relatively a long time to reach equilibrium for the sorption of analytes from gas phase onto the metal oxides, especially for porous materials. The dependency of the resistance of the metal oxides on the vapor concentration is not linear, which reduces the accuracy of quantitative analysis (Simon et al. *J. Comb. Chem.*, 2002, 4, 511-515). Some metal oxides work only at temperatures higher than a "switch on" value, e.g. >700° C. for $SrTiO_3$ (Hu et al., *J. Phys. Chem.* B; 2004, 108, 11214-11218; Wang et al., *J. Am. Chem. Soc.*, 2003, 125, 16176-16177; Dutta et al., *Chem. Mater.*, 2004, 16, 5198-5204).

Rubbery polymers with low glass transition temperatures ($T_g$) have been used as coatings for detection of nonpolar or weakly polar organic vapors (Grate et al., *Anal. Chem.*, 1993, 65, 987A). The vapor sorption in rubbery polymers is reversible and equilibrium is attained rapidly (Grate et al., *Anal. Chem.*, 1993, 65, 987A; (a) Jarrett and Finklea, *Anal. Chem.*, 1999, 71, 353; (b) Shinar et al., *Anal. Chem.*, 2000, 72, 5981; (c) Zellers et al., *Anal. Chem.*, 1995, 67, 1092; (d) Patrash and Zellers, *Anal. Chem.*, 1993, 65, 2055). However, the mechanical properties of rubbery polymers strongly depend upon temperature (U. W. Gedde, *Polymer Physics*, Kluwer Academic Publ., Doedrecht, Netherlands, 1999). Most polymer materials with low $T_g$ are not stable at high temperatures. Therefore, applications of polymer materials for high temperature vapor sensing are limited. Furthermore, if the vapors cannot absorb on the materials, the large surface-area to volume ratio sensing materials, such as graphite ((a) Jarrett and Finklea, *Anal. Chem.*, 1999, 71, 353; (b) Shinar et al., *Anal. Chem.*, 2000, 72, 5981; (c) Zellers et al., *Anal. Chem.*, 1995, 67, 1092; (d) Patrash and Zellers, *Anal. Chem.*, 1993, 65, 2055) or oxides (Dutta et al., *J. Phys. Chem.* B, 1999, 103, 4412-4422; Ikohura and Watson, *The Stannic Oxide Gas Sensor*; CRC Press: Boca Raton, Fla., 1994; Zhu et al., *Anal. Chem.*, 2002, 74, 120-124) would not work for high temperature gas sensing.

U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, and U.S. Pat. No. 6,087,187 to Wiegland et al. each teach using a piezoelectric sensor for the detection of an analyte in a liquid sample. U.S. Patent Application Publication Nos. 2003/0077222, 2003/0073133, 2003/0072710, 2003/0068273, 2003/0053950, and 2003/0049204, all to Leyland-Jones, discloses immunosensors which in particular embodiments have antibodies, Fab fragments, or scFv polypeptides immobilized on the surface thereof.

U.S. Patent Application Nos. 2002/0094531 to Zenhausern teach sensing probes such as a QCM for detecting a biological analyte of interest in gaseous, vapor, or liquid forms. The sensing probes are coated with various materials, such as polymers, ion exchange resins, porous silicon, silanes, thiols, and oxides. However ionic liquids are not taught as a coating for the sensing probes.

U.S. Patent Application Nos. 2002/0142477 to Lewis et al. teach organic vapor measurement using a polymer-coated quartz crystal microbalance. The quartz crystal microbalance crystals are coated with polymers including poly (ethylene-co-vinyl acetate) with 25% acetate (PEVA) and poly(caprolactone) (PCL) polymer films.

Liang et al. (*Anal. Chem.*, 2002, 74, pp. 2172-2176) teach a quartz crystal microbalance device which employs an ionic liquid for sensing organic vapors. Liang et al. used an ionic liquid having $1-R_1-2-R_2$-3-methylimidazolium cations where $R_1$ is ethyl, propyl, or butyl and $R_2$ is H or methyl in a system which operated at a constant temperature of 25° C. The QCM sensors coated with the ionic liquids had a linear response only in the narrow concentration range from $2.3 \times 10^4$ to $3.8 \times 10^5$ ppm. The linearity of the frequency shift versus the concentration did not extend to low concentrations or high concentrations.

While the related art teach gas sensors and piezoelectric sensors for detecting analytes in liquids, there still exists a need for a superior gas sensor which are capable of detecting both polar and nonpolar organic vapors at high temperature which have a fast linear and reversible response.

OBJECTS

Therefore, it is an object of the present invention to provide ionic liquid piezoelectric gas sensors.

It is further an object of the present invention to provide ionic liquid piezoelectric gas sensors which are capable of detecting both polar and nonpolar organic vapors at high temperatures.

It is still further an object of the present invention to provide gas sensors which have a fast linear and reversible response.

These and other objects will become increasingly apparent by reference to the following description.

SUMMARY OF THE INVENTION

The present invention provides an ionic liquid high temperature piezoelectric gas sensor for determining the concentration of an organic vapor in a gaseous sample comprising: a quartz crystal microbalance having a transducer surface; and an ionic liquid film on the transducer surface of the quartz crystal microbalance, wherein when the organic vapor is present in the gaseous sample it is absorbed in the ionic liquid film on the transducer surface and changes a resonant frequency of the quartz crystal microbalance proportional to the concentration of the organic vapor in the gaseous sample. In further embodiments, the ionic liquid film has a thickness of about 25 µg cm$^{-2}$ or less. In further embodiments the ionic liquid is phosphonium dodecylbenzene-sulfonate. In still further embodiments the phosphonium dodecylbenzene-sulfonate is $P_{6,6,6,14}DBS$.

The present invention provides a method of determining the concentration of an organic vapor in a high temperature gaseous sample comprising: providing an ionic liquid piezoelectric gas sensor for detecting the presence of an organic vapor in a gaseous sample comprising a quartz crystal microbalance having a transducer surface, and an ionic liquid film on the transducer surface of the quartz crystal microbalance, wherein when the organic vapor is present in the gaseous sample it is absorbed in the ionic liquid film on the transducer surface and changes a resonant frequency of the quartz crystal microbalance; providing the high temperature gaseous sample to the transducer surface of the ionic liquid piezoelectric gas sensor; measuring a change in the resonant frequency of the piezoelectric mass sensor upon stabilization of the resonant frequency; and determining the concentration of the organic vapor in the gaseous sample by the change in the resonant frequency. In further embodiments, the ionic liquid film has a thickness of about 25 µg cm$^{-2}$ or less. In further embodiments the ionic liquid is phosphonium dodecylbenzene-sulfonate. In still further embodiments the phosphonium dodecylbenzene-sulfonate is $P_{6,6,6,14}DBS$.

The present invention provides a method of determining the concentration of an organic vapor in a high temperature gaseous sample comprising: providing an ionic liquid piezoelectric gas sensor for detecting the presence of an organic vapor in a gaseous sample comprising a quartz crystal microbalance having a transducer surface, and an ionic liquid film on the transducer surface of the quartz crystal microbalance, wherein when the organic vapor is present in the gaseous sample it is absorbed in the ionic liquid film on the transducer surface and changes a resonant frequency of the quartz crystal microbalance; providing a high temperature reference gas to the transducer surface of the ionic liquid piezoelectric gas sensor; measuring a reference frequency of the gas sensor; providing the high temperature gaseous sample to the transducer surface of the ionic liquid piezoelectric gas sensor; measuring a second resonant frequency of the gas sensor; subtracting the first resonant frequency from the second resonant frequency to provide a frequency change; and determining the concentration of the organic vapor in the gaseous sample by the frequency change. In further embodiments, the ionic liquid film has a thickness of about 25 µg cm$^{-2}$ or less. In further embodiments the ionic liquid is phosphonium dodecylbenzene-sulfonate. In still further embodiments the phosphonium dodecylbenzene-sulfonate is $P_{6,6,6,14}DBS$.

The present invention provides a method of determining the concentration of an organic vapor in a high temperature gaseous sample comprising: providing a first ionic liquid piezoelectric gas sensor and a second ionic liquid piezoelectric gas sensor, the first and second ionic liquid piezoelectric gas sensors each comprising a quartz crystal microbalance having a transducer surface, and an ionic liquid film on the transducer surface of the quartz crystal microbalance, wherein when the organic vapor is present in the gaseous sample it is absorbed in the ionic liquid film on the transducer surface and changes a resonant frequency of the quartz crystal microbalance; providing a high temperature reference gas to the first gas sensor; providing the high temperature gaseous sample to the second gas sensor; measuring a resonant frequency of the first sensor; measuring a resonant frequency of the second sensor; and subtracting the resonant frequency of the first sensor from the resonant frequency of the second sensor to provide a frequency difference; and determining the concentration of the organic vapor in the gaseous sample by the frequency difference. In further embodiments, the ionic liquid film has a thickness of about 25 µg cm$^{-2}$ or less. In further embodiments the ionic liquid is phosphonium dodecylbenzene-sulfonate. In still further embodiments the phosphonium dodecylbenzene-sulfonate is $P_{6,6,6,14}DBS$.

The present invention provides a method of determining a Henry constant of an organic compound in an ionic liquid comprising: providing an ionic liquid high temperature piezoelectric gas sensor comprising a quartz crystal microbalance having a transducer surface and an ionic liquid film on the transducer surface of the quartz crystal microbalance; providing the organic compound at a partial pressure ($p_i$) in a high temperature gaseous sample to the transducer surface of the ionic liquid piezoelectric gas sensor; measuring a change in the resonant frequency of the piezoelectric mass sensor upon stabilization of the resonant frequency; calculating a molar fraction ($m_i$) of the organic compound in the ionic liquid using Sauerbrey's equation from the change in the resonant frequency and total mass of the ionic liquid film on the transducer surface; determining the Henry constant ($C_i$) of the organic compound in the gaseous sample using equation $p_i = C_i m_i$, from the partial pressure ($p_i$) and the molar fraction ($m_i$) of the organic compound. In further embodiments, the ionic liquid film has a thickness of about 25 µg cm$^{-2}$ or less. In further embodiments, the ionic liquid is phosphonium dodecylbenzene-sulfonate. In further embodiments, the phosphonium dodecylbenzene-sulfonate is $P_{6,6,6,14}DBS$.

DETAILED DESCRIPTION OF THE INVENTION

Figure 1:
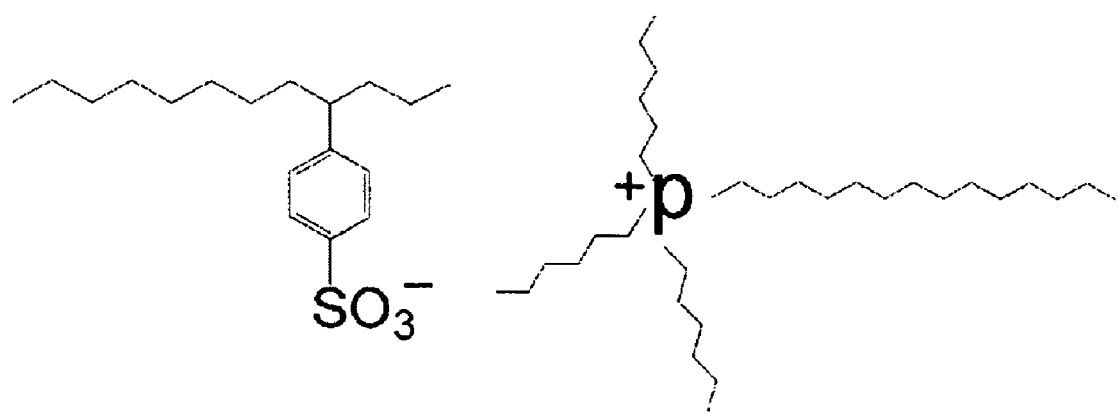
FIG. 1 illustrates the structure of IL $P_{6,6,6,14}DBS$.

All patents, patent applications, government publications, government regulations, and literature references cited in this specification are hereby incorporated herein by reference in their entirety. In case of conflict, the present description, including definitions, will control.

The term "high temperature" as used herein refers to temperatures greater than 100° C.

The term "QCM" as used herein refers to a quartz crystal microbalance. Quartz crystal microbalance devices which can be used in the present invention include QCM devices available from Maxtek Inc. of Santa Fe Springs, Calif. Other QCM devices which can be used in the present invention are described in U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al., U.S. Pat. No. 6,890,486 to Penelle, U.S. Pat. No. 6,848,299 to Paul et al., U.S. Pat. No. 6,706,977 to Cain et al., U.S. Pat. No. 6,647,764 to Paul et al., U.S. Pat. No. 6,492,601 to Cain et al., U.S. Pat. No. 6,439,765 to Smith, U.S. Pat. No. 6,190,035 to Smith, U.S. Pat. No. 6,106,149 to Smith, U.S. Pat. No. 5,885,402 to Esquibel, U.S. Pat. No. 5,795,993 to Pfeifer et al., U.S. Pat. No. 5,706,840 to Schneider, U.S. Pat. No. 5,616,827 to Simmermon et al., U.S. Pat. No. 5,484,626 to Storjohann et al., U.S. Pat. No. 5,282,925 to Jeng et al., U.S. Pat. No. 5,233,261 to Wajid, U.S. Pat. No. 5,201,215 to Granstaff et al., U.S. Pat. No. 4,999,284 to Ward et al., and U.S. Pat. No. 4,788,466 to Paul et al. Examples of control circuitry for quartz crystal microbalances and methods for detecting materials using piezoelectric resonators are described in U.S. Pat. No. 5,117,192 to Hurd and U.S. Pat. No. 5,932,953 to Drees et al. Some methods which have been used to attach substances to surfaces such as the receptor surfaces of the QCM are described in U.S. Pat. No. 6,475,809 to Wagner et al., U.S. Pat. No. 6,475,808 to Wagner et al., U.S. Pat. No. 6,368,877 to Zhang et al., U.S. Pat. No. 6,319,674 B1 to Fulcrand et al., and U.S. Pat. No. 5,622,826 to Varma, and Yang et al., Nature Materials 1: 253-257 (2002). Each of the above references are hereby incorporated herein by reference in their entirety.

The term "organic vapor" as used herein refers to gaseous phase organic molecules. The term encompasses both polar organic molecules (including, but not limited to ethanol and dichloromethane) and nonpolar organic molecules (including, but not limited to heptane and benzene).

The term "ionic liquid" as used herein refers to a liquid salt consisting solely of ions. Preferably the ionic liquids are room-temperature ionic liquids (RTILs) which melt at or close to room temperature, and typically they are salts whose melting point is below approximately 100° C. Preferably the ionic liquids have negligible vapor pressure and have high thermal stability. The term ionic liquid (IL) encompasses liquids having organic cations and anions. They typically comprise bulky asymmetric organic cations such as 1-alkyl-3-methylimidazolium, 1-alkylpyridinium, N-methyl-N-alkylpyrrolidinium or ammonium ions and a wide range of anions. Preferred ionic liquids are phosphonium salts. Phosphonium salts are more thermally stable than the corresponding ammonium salts and imidazolium salts. While the use of phosphonium dodecylbenzene-sulfonate, specifically $P_{6,6,6,14}$DBS, is described herein other ionic liquids can be used. Examples of some ionic liquids useful for the present invention and their production are described in U.S. Pat. No. 6,852,229 to Mehnert et al., U.S. Patent Application Publication No. 2003/0204041 to Laas et al., U.S. Patent Application Publication No. 2004/0054231 to Abbott et al., U.S. Patent Application Publication No. 2004/0262578 to Wasserscheid et al., and U.S. Patent Application Publication No. 2005/0005840 to Bonrath et al. hereby incorporated herein by reference in their entirety.

Room-temperature ionic liquids (ILs) are a relatively new class of compounds containing organic cations and anions, which melt at or close to room temperature. ILs show great promises as gas sensing materials (K. R. Seddon, *J. Chem Tech. Biotech.*, 1997, 68, 315-316). ILs have negligible vapor pressure and many possess high thermal stability (Z. Zhang and R. G. Reddy, EPD congress 2002, P. R. Taylor, Ed., TMS, Warrendale, Pa., 2002, p. 199). Most ILs show typical decomposition temperatures of 350+° C. The remarkable thermal stability has important implications in the use of ILs for high temperature gas sensing.

Figure 2:
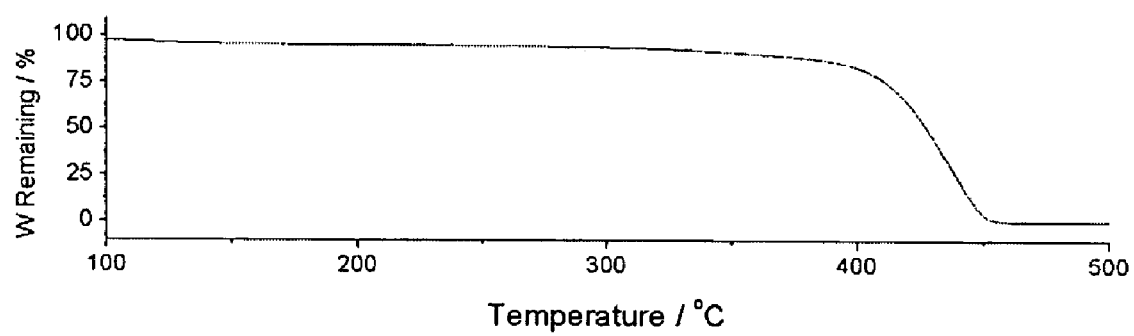
FIG. 2 is a graph showing the TGA curve of $P_{6,6,6,14}DBS$.

IL high temperature piezoelectric gas sensors using phosphonium dodecylbenzene-sulfonate (i.e. $P_{6,6,6,14}$DBS) as sensing materials coated on quartz crystal microbalance (QCM) transducers are provided. QCM is a mass sensor and has been used for organic vapor detection at room temperature ((a) G. Sauerbrey, *Z. Phys.*, 1959, 155, 206; (b) M. Albrecht, M. Schlupp, J. Bargon and G. van Koten, *Chem. Commun.*, 2001, 1874). $P_{6,6,6,14}$DBS, the structure of which is illustrated in FIG. 1, was prepared via an alcohol-to-alkyl halide conversion method ((a) R. X. Ren and J. X. Wu, *Org. Lett.*, 2001, 3, 3727; (b) R. X. Ren and A. Robertson, WO 0351894, 2003.), a simple one-pot synthesis. The structural data of $P_{6,6,6,14}$DBS is as follows: Proton NMR (in $CDCl_3$, Hz) 7.86 (d, 2H, 8 Hz), 7.07 (dd, 2H, 8 Hz), 2.62 (tt, 1H, 5 Hz), 2.28 (m, 8H), 1.46 (m, 20H), 1.23 (m, 40H), 0.85 (m, 16H), 0.8 (t, 3H, 5 Hz), 0.75 (t, 3H, 5 Hz). ES-MS: anion m/z 5 325.18 (calcd 325.49), cation m/z 5 483.4 (calcd 483.86). FTIR (cm21): 2956, 2929, 2860, 1668, 1597, 1464, 1376, 1205, 1035, 1010, 832. TGA study shows it is thermally stable up to 350° C., as illustrated in the graph of FIG. 2. The IL/QCM sensor has a fast and reversible response to various organic vapors at high temperature.

The $P_{6,6,6,14}$DBS was coated on the QCM from its dichloromethane solution. Typically, the surface loading of the IL was ca. 17 μg $cm^{-2}$ in the embodiments described herein. Ultra thin films with thickness less than tens of nanometers (nm) are more rigid and will have little shear modulus change upon vapor sorption (J. W. Grate, S. J. Martin and R. M. Write, *Anal. Chem.*, 1993, 65, 987A; J. W. Grate and M. Klusty, *Anal. Chem.*, 1991, 63, 1719). Preferably the thin films have a thickness of 100 nm or less. The $P_{6,6,6,14}$DBS/QCM sensor for detection of various organic vapors was studied at elevated temperatures controlled by a gas chromatograph (GC) oven. The test vapors were diluted by the pure nitrogen carrier gas and the carrier concentrations of the vapors were controlled by two mass-flow controllers (MKS Instruments, Inc., Wilmington, Mass.).

Figure 3:
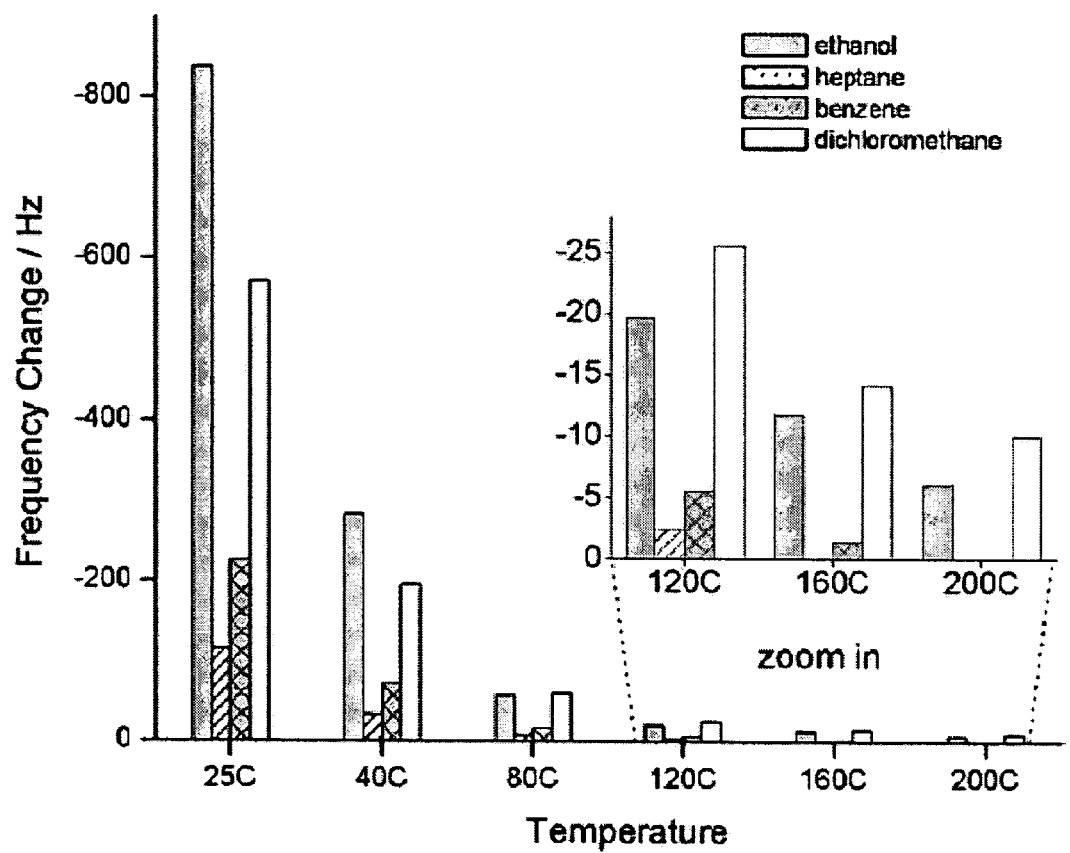
FIG. 3 is a graph showing the frequency change of the IL/QCM sensor exposed to ethanol, heptane, benzene and dichloromethane at various temperatures. The same concentration was used for the vapors and all temperatures.

As shown in FIG. 3, upon exposure of $P_{6,6,6,14}$DBS/QCM sensor to both polar (ethanol or dichloromethane) and nonpolar (heptane or benzene) organic vapors, a decrease of the resonance frequency of the QCM was observed over a range from room temperature to as high as 200° C. On bare QCM, the frequency shift was very small. As expected by thermodynamics, the frequency change decreased exponentially with increasing temperature. $P_{6,6,6,14}$DBS is polar, consequently, greater sensitivity was observed for ethanol and dichloromethane (polar) than that of heptane and benzene (nonpolar) at all temperatures.

TABLE 1

Frequency change (Hz) when bare QCM and IL/QCM exposed to $N_2$ flow containing 110 mg $L^{-1}$ ethanol vapor.

| | T/° C. | | | | | |
|---|---|---|---|---|---|---|
| | 24 | 40 | 80 | 120 | 160 | 200 |
| On Bare QCM | 36 | 10.4 | 3.9 | 1.4 | — | — |
| On QCM/IL | 836 | 284 | 57.4 | 19.7 | 11.9 | 6.2 |

Table 1 shows the data summary for both $P_{6,6,6,14}$DBS/QCM and the bare QCM response to 110 mg $L^{-1}$ ethanol vapor at elevated temperatures. Not only does the IL/QCM show a higher sensitivity at all temperatures than the bare QCM, but also these data illustrate that the IL/QCM can be used as a gas sensing device at high temperatures. When the system was cooled down to 24° C., the IL/QCM sensor gave reproducible response at 24° C. again indicating high stability and reversibility. At temperature much higher than the boiling point, very few vapor molecules can be adsorbed on solid surfaces. Consequently, the sensors can be regenerated by raising the temperature to desorb other impurities without affecting the IL film. The ionic liquid film thickness effect was also studied. When IL films thickness is between 0-25 μg $cm^{-2}$, the frequency change increased linearly with the film thickness. However, increased frequency change was not observed at larger IL thickness than 25 μg $cm^{-2}$.

Figure 4:
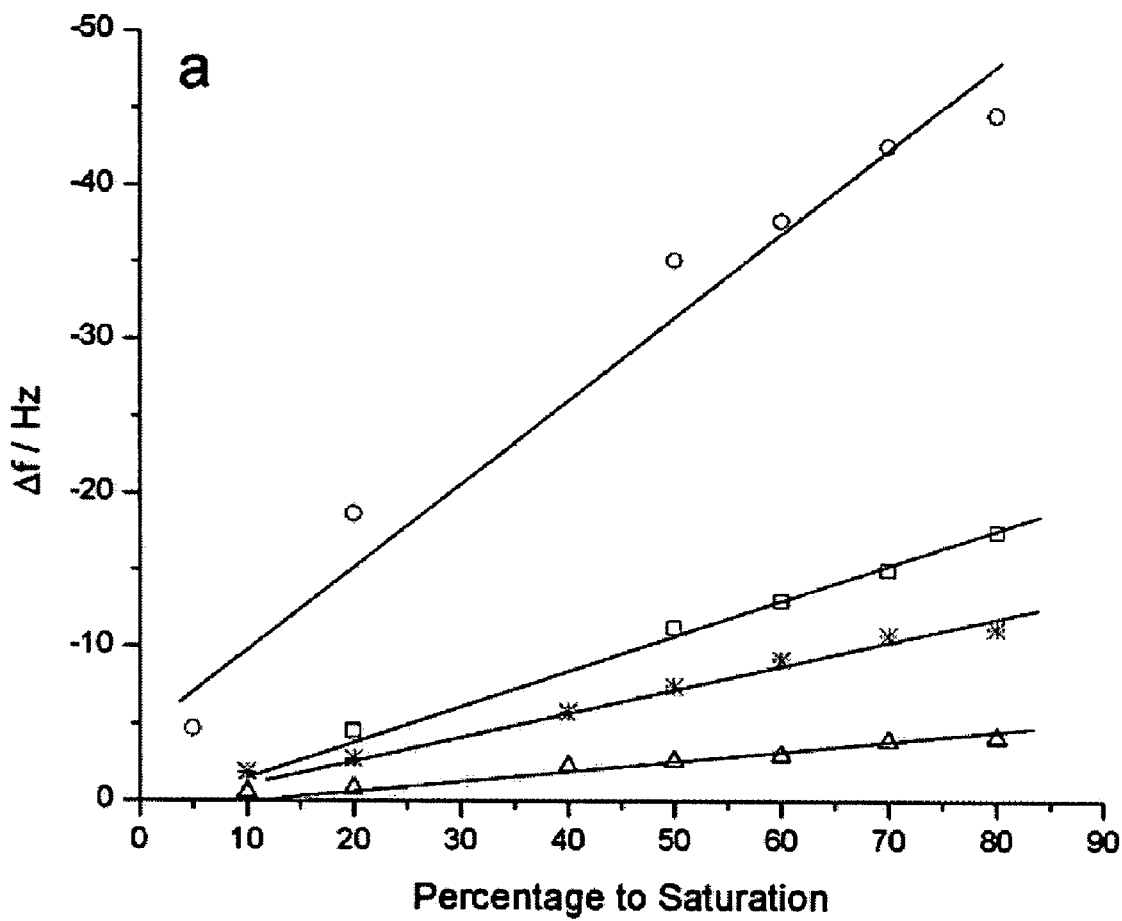
FIG. 4 is a graph showing frequency change, Δf (Hz) vs. concentration (percentage to saturation) of the IL/QCM sensor exposed separately to ethanol (square), heptane (triangle), benzene (star) and dichloromethane (circle) at 120° C.
Figure 5:
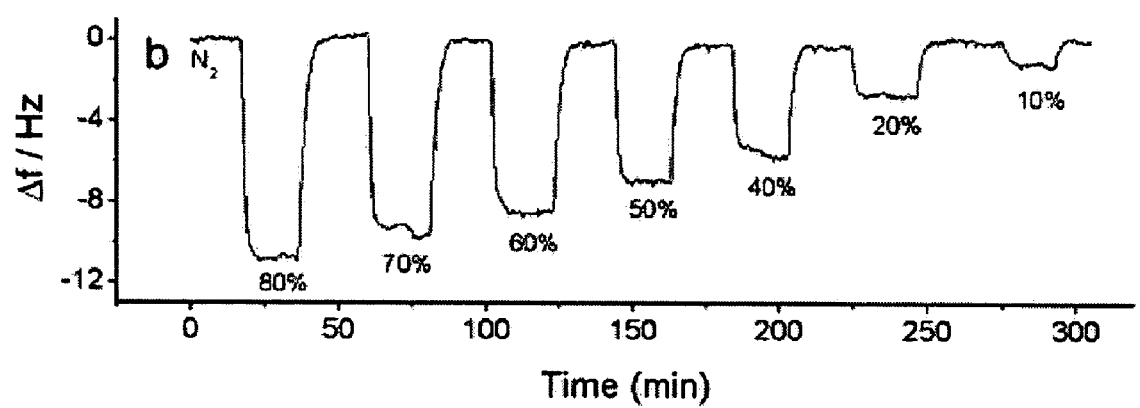
FIG. 5 is a graph of frequency change, Δf (Hz) illustrating the sensorgram of benzene at 120° C. from various concentrations.

As shown in FIG. 4, a linear relationship of the frequency changes and the concentrations of vapor were obtained over the 0% to 100% saturation vapor pressure range at 120° C. for all four organic vapors tested. (Note: 100% is when the $N_2$ flow was saturated with the sample vapor at 24° C., the other percentage is obtained by dilution using the second pure $N_2$ flow.) The detection limit could reach as low as 5%, which equals to 7 mg $L^{-1}$, ethanol, 12 mg $L^{-1}$, heptane, 21 mg $L^{-1}$, benzene and 100 mg $L^{-1}$, dichloromethane. FIG. 5 is the sensorgram of benzene at 120° C. showing excellent reversibility of the absorption/desorption processes. This characteristic eliminates the need to purge the system to regenerate the sensing sites before each measurement, which assures real-time monitoring. Each time the sample channel was switched on or off, a constant frequency was established in a few minutes. Since a very slow flow rate of the carrier gas 30 ml $min^{-1}$ was used to minimize the mechanical vibration of the QCM, it took several minutes to fill or purge off the sensor chamber, which is ca. 150 ml in volume. So the time to reach constant frequency is not the equilibrium time of absorption or desorption. It was found that the solubility equilibrium of organic vapors in ILs could be reached in a few seconds (C. Liang, C. Y. Yuan, R. J. Warmack, C. E. Barnes and S. Dai, *Anal. Chem.*, 2002, 74, 2172.). The response time and the sensitivity depend also on the boiling point of the organic samples (J. W. Grate, M. Klusty, R. A. Mcill, M. H. Abraham, G. Whiting and J. Andonian-Haftvan, *Anal. Chem.*, 1992, 64, 610). When the flow rate was increased, the response time decreased, while the frequency change did not depend on the flow rate.

Several factors may cause the frequency change of the QCM upon absorption of organic vapors into IL film. At an ideal condition, the frequency change is only caused by the mass loading on the surface. To evaluate mass loading effects experimentally, an equation was derived, from the Sauerbrey equation (G. Sauerbrey, *Z. Phys.*, 1959, 155, 206; M. Albrecht, M. Schlupp, J. Bargon and G. van Koten, *Chem. Commun.*, 2001, 1874), relating sensor responses to partition coefficients: $\Delta f_{v(mass)} = \Delta f_n C_v K/\rho$, where $\Delta f_{v(mass)}$, $\Delta f_n$, $C_v$, K and ρ are, respectively, the frequency shift caused by the adsorption of the vapor, the coating thickness in kHz, the vapor concentration in the gas phase, the partition coefficient and the coating material's density. However, reports show that both the mass loading and the viscosity change of the IL film upon the absorption of vapors can cause the frequency change at room temperature (C. Liang, C. Y. Yuan, R. J. Warmack, C. E. Barnes and S. Dai, *Anal. Chem.*, 2002, 74, 2172). The change of the viscosity or modulus of the coating is reflected by the change of damping resistance fitted by the BVD circuit (A. Janshoff, H. Galla and C. Steinem, *Angew Chem. Int. Ed.*, 2000, 39, 4004-4032). The damping resistance and the frequency change were measured simultaneously during the vapor detection experiments using Maxtek® Research Quartz Crystal Microbalance (RQCM) (Santa Fe Springs, Calif.).

TABLE 2

Value of damping resistances and their changes during experiments

| | 24° C. | | 40° C. | | 80° C. | | 120° C. | |
|---|---|---|---|---|---|---|---|---|
| | R (Ω) | ΔR % | R (Ω) | ΔR % | R (Ω) | ΔR % | R (Ω) | ΔR % |
| Ethanol | 4.7 | ±11% | 3.9 | ±2.6% | 4.0 | ±1.9% | 4.4 | ±0.7 |
| Benzene | 3.3 | ±3.7% | 3.4 | ±2.2% | 3.4 | ±1.1% | 3.6 | ±1.4% |
| Heptane | 3.2 | ±1.6% | 3.1 | ±1.3% | 3.2 | ±1.2% | 3.4 | ±1.5% |
| Dichloromethane | 3.5 | ±12% | 3.5 | ±7.1% | 3.6 | ±3.3% | 3.9 | ±2.6% |

Table 2 summarized the data of damping resistance (R) and its change (ΔR %) for the four samples at different temperatures. At room temperature, the ΔR % values are relatively large, e.g. 11% for ethanol and 12% for dichloromethane, indicating a big viscosity change of the film upon the absorption of organic vapors. This agrees with the previous report at room temperature (C. Liang, C. Y. Yuan, R. J. Warmack, C. E. Barnes and S. Dai, *Anal. Chem.*, 2002, 74, 2172). However, at higher temperature, the ΔR % values decreased. At 120° C., it is less than 2.6% for the four samples tested due to the smaller amount of vapors absorbed in the IL film at high temperature. Consequently, the change of viscosity caused by the gas adsorption on the IL film is very small at high temperature, and hence, the frequency changes were contributed mainly from the mass loading in the IL film and the Sauerbrey equation relating frequency change to pure mass loading is valid. At high temperature, the Δf vs. C curve also mirrors the Henry's gas law (G. R. Mortimer, *Physical Chemistry*, 2nd edition, Academic Press, San Diego, Calif., 2000, p. 210) (i.e., the concentration of a gas sample in liquid solvent is proportional to the concentration (or the partial pressure) of the sample in gas phase). Consequently, Henry constants can be measured with good accuracy at high temperature by IL/QCM sensors. The Henry constants of the four samples in IL $P_{6,6,6,14}$DBS at 120° C. were calculated to be $3.49 \times 10^5$ Pa, ethanol, $1.52 \times 10^4$ Pa, benzene, $1.95 \times 10^6$ Pa, dichloromethane and $2.01 \times 10^6$ Pa, heptane according to equation 5 $p_j = C_i m_i$, where $p_i$ is the partial pressure of the samples in gas phase, $C_i$ is the Henry constant and $m_i$ is the molar fraction of the samples in the IL. Saturated vapor pressures were obtained from vapor pressure data (S. Ohe, http://www.s-ohe.com). $m_i$ was calculated from Sauerbrey equation (for 10 MHz crystal, the sensitivity is 1.02 ng cm$^{-2}$ Hz$^{-1}$) and the total weight of the IL film is 17 μg cm$^{-2}$.

Figure 6:
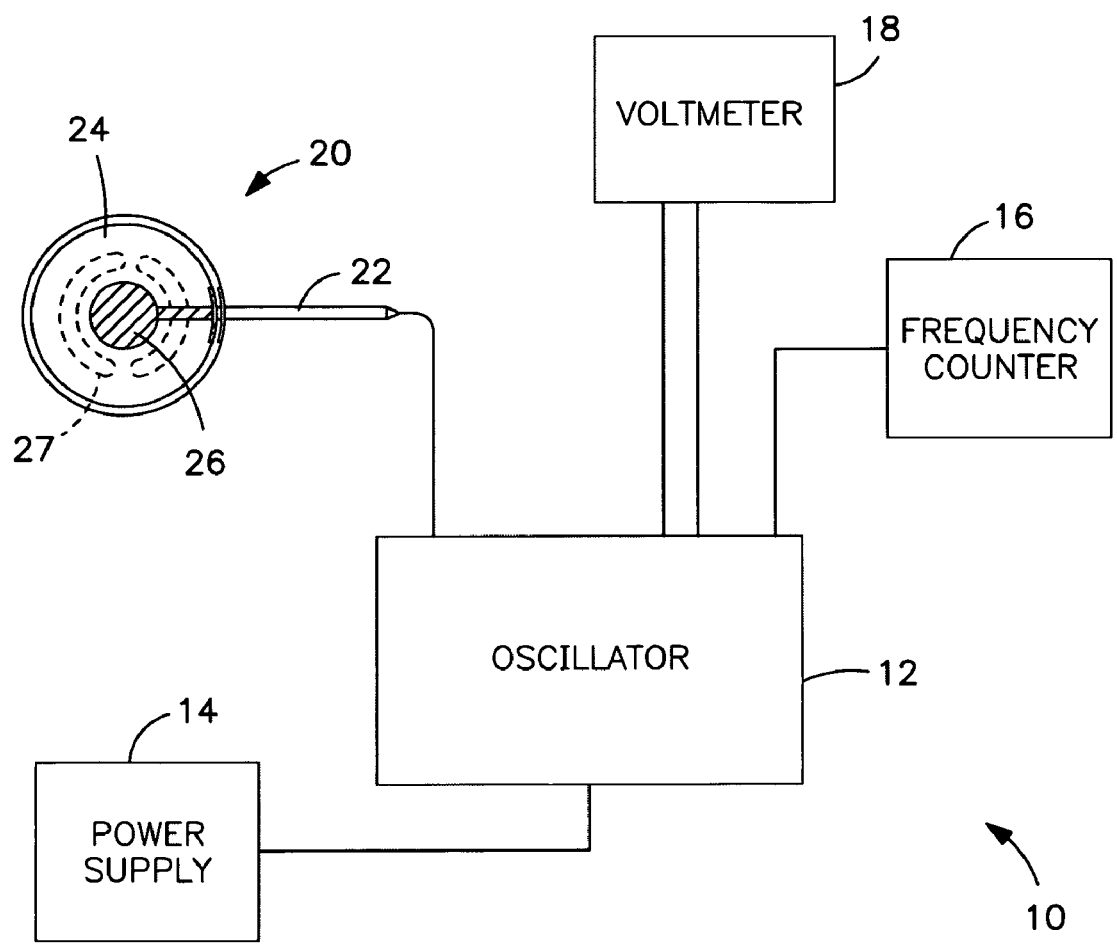
FIG. 6 is a schematic diagram of one embodiment of a crystal measurement system 10 for the ionic liquid piezoelectric gas sensor 20 of the present invention.

The Maxtek® RQCM crystal measurement system was used for the vapor detection experiments described herein, however any crystal measurement system can be used. The Maxtek® RQCM system provides data logging and analysis software, analog and digital inputs, temperature inputs, and relay outputs. The Maxtek® RQCM can be used with Maxtek® one inch (2.54 cm) diameter crystals with an optional Maxtek® FC-550 flow cell to the Maxtek® crystal holder for use as a low volume flow cell, however other crystals and holders can be used. Alternatively a Maxtek® PLO-10 phase lock oscillator can be used as a stand alone crystal oscillator used in conjunction with any frequency counter and voltmeter for data acquisition for the present invention. While Maxtek® crystal measurement systems are used in the present example, any other comparable system can be utilized with the present invention. One possible configuration of the crystal measurement system 10 for use with the ionic liquid piezoelectric gas sensor 20 is illustrated in FIG. 6. In this configuration, a quartz crystal 24 is held in a crystal holder 22 during analysis of a gas sample. A sensing electrode 26 having an ionic liquid film, and a contact electrode 27 provide electrical connections to supply an output signal from the quartz crystal 24 to an oscillator 12. The oscillator 12 having a power supply 14 drives the quartz crystal 24 of the ionic liquid piezoelectric gas sensor 20. A frequency counter 16 and a voltmeter 18 are connected to the oscillator 12 to display the results derived from the output signal of the quartz crystal 24.

The ionic liquid piezoelectric gas sensor of the present invention detects both polar and nonpolar organic vapors at high temperature. The sensor gives linear, fast and reversible response at temperatures up to 200° C. In particular, at high temperatures, the sensor response to the partial pressure of the gas sample is linear and abides by the Sauerbrey equation. Ionic liquids offer many options for chemical modifications and hence a huge flexibility in tailoring molecular recognition sites by controlled organic synthesis and surface designs. This provides an exciting opportunity to explore their application not only in high temperature gas sensing but also in highly sensitive and selective detection for trace analytes using IL sensor array.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. An ionic liquid high temperature piezoelectric gas sensor for determining the concentration of an organic vapor in a gaseous sample comprising:
   (a) a quartz crystal microbalance having a transducer surface; and
   (b) an ionic liquid film on the transducer surface of the quartz crystal microbalance, the ionic liquid comprising a phosphonium salt;
   wherein when the organic vapor is present in the gaseous sample it is absorbed in the ionic liquid film on the transducer surface and changes a resonant frequency of the quartz crystal microbalance proportional to the concentration of the organic vapor in the gaseous sample.

2. The ionic liquid high temperature piezoelectric gas sensor of claim 1, wherein the ionic liquid film has a thickness of about 25 μg cm$^{-2}$ or less.

3. The ionic liquid high temperature piezoelectric gas sensor of claim 1, wherein the ionic liquid is phosphonium dodecylbenzene-sulfonate.

4. The ionic liquid high temperature piezoelectric gas sensor of claim 3, wherein the phosphonium dodecylbenzene-sulfonate is $P_{6,6,6,14}$DBS.

5. A method of determining the concentration of an organic vapor in a high temperature gaseous sample comprising:
   (a) providing an ionic liquid high temperature piezoelectric gas sensor for detecting the concentration of an organic vapor in a gaseous sample, the gas sensor comprising a quartz crystal microbalance having a transducer surface and an ionic liquid film on the transducer surface of the quartz crystal microbalance, wherein (i) the ionic liquid comprises a phosphonium salt and (ii) when the organic vapor is present in the gaseous sample it is absorbed in the ionic liquid film on the transducer surface and changes a resonant frequency of the quartz crystal microbalance;
   (b) providing the high temperature gaseous sample to the transducer surface of the ionic liquid piezoelectric gas sensor;
   (c) measuring a change in the resonant frequency of the piezoelectric mass sensor upon stabilization of the resonant frequency; and
   (d) determining the concentration of the organic vapor in the gaseous sample by the change in the resonant frequency.

6. The method of claim 5, wherein the ionic liquid film has a thickness of about 25 μg cm$^{-2}$ or less.

7. The method of claim 5, wherein the ionic liquid is phosphonium dodecylbenzene-sulfonate.

8. The method of claim 7 wherein the phosphonium dodecylbenzene-sulfonate is $P_{6,6,6,14}$DBS.

9. A method of determining the concentration of an organic vapor in a high temperature gaseous sample comprising:
   (a) providing an ionic liquid high temperature piezoelectric gas sensor for detecting the concentration of an organic vapor in a gaseous sample, the gas sensor comprising a quartz crystal microbalance having a transducer surface and an ionic liquid film on the transducer surface of the quartz crystal microbalance, wherein (i) the ionic liquid comprises a phosphonium salt and (ii) when the organic vapor is present in the gaseous sample it is absorbed in the ionic liquid film on the transducer surface and changes a resonant frequency of the quartz crystal microbalance;
   (b) providing a high temperature reference gas to the transducer surface of the ionic liquid piezoelectric gas sensor;
   (c) measuring a first reference frequency of the gas sensor;
   (d) providing the high temperature gaseous sample to the transducer surface of the ionic liquid piezoelectric gas sensor;
   (e) measuring a second resonant frequency of the gas sensor;

(f) subtracting the first resonant frequency from the second resonant frequency to provide a frequency change; and (g) determining the concentration of the organic vapor in the gaseous sample by the frequency change.

10. The method of claim 9, wherein the ionic liquid film has a thickness of about 25 μg cm$^{-2}$ or less.

11. The method of claim 9, wherein the ionic liquid is phosphonium dodecylbenzene-sulfonate.

12. The method of claim 11, wherein the phosphonium dodecylbenzene-sulfonate is $P_{6,6,6,14}$DBS.

13. A method of determining the concentration of an organic vapor in a high temperature gaseous sample comprising:

(a) providing a first ionic liquid piezoelectric gas sensor and a second ionic liquid piezoelectric gas sensor, the first and second ionic liquid high temperature piezoelectric gas sensor for detecting the concentration of an organic vapor in a gaseous sample comprising a quartz crystal microbalance having a transducer surface, and an ionic liquid film on the transducer surface of the quartz crystal microbalance, wherein (i) the ionic liquid comprises a phosphonium salt and (ii) when the organic vapor is present in the gaseous sample it is absorbed in the ionic liquid film on the transducer surface and changes a resonant frequency of the quartz crystal microbalance;

(b) providing a high temperature reference gas to the first gas sensor;

(c) providing the high temperature gaseous sample to the second gas sensor;

d) measuring a resonant frequency of the first sensor;

(e) measuring a resonant frequency of the second sensor;

(f) subtracting the resonant frequency of the first sensor from the resonant frequency of the second sensor to provide a frequency difference; and (g) determining the concentration of the organic vapor in the gaseous sample by the frequency difference.

14. The method of claim 13, wherein the ionic liquid film has a thickness of about 25 μg cm$^{-2}$ or less.

15. The method of claim 13, wherein the ionic liquid is phosphonium dodecylbenzene-sulfonate.

16. The method of claim 15, wherein the phosphonium dodecylbenzene-sulfonate is $P_{6,6,6,14}$DBS.

17. A method of determining a Henry constant of an organic compound in an ionic liquid comprising:

(a) providing an ionic liquid high temperature piezoelectric gas sensor comprising a quartz crystal microbalance having a transducer surface and a film of the ionic liquid on the transducer surface of the quartz crystal microbalance, wherein the ionic liquid comprises a phosphonium salt;

(b) providing the organic compound at a partial pressure ($p_i$) in a high temperature gaseous sample to the transducer surface of the ionic liquid piezoelectric gas sensor;

(c) measuring a change in the resonant frequency of the piezoelectric mass sensor upon stabilization of the resonant frequency;

(d) calculating a molar fraction ($m_i$) of the organic compound in the ionic liquid using Sauerbrey's equation from the change in the resonant frequency and total mass of the ionic liquid film on the transducer surface;

(e) determining the Henry constant ($C_i$) of the organic compound in the gaseous sample using equation $p_i = C_i m_i$, from the partial pressure ($p_i$) and the molar fraction ($m_i$) of the organic compound.

18. The method of claim 17, wherein the ionic liquid film has a thickness of about 25 μg cm$^{-2}$ or less.

19. The method of claim 17, wherein the ionic liquid is phosphonium dodecylbenzene-sulfonate.

20. The method of claim 19, wherein the phosphonium dodecylbenzene-sulfonate is $P_{6,6,6,14}$DBS.

* * * * *